(12) United States Patent
Latta

(10) Patent No.: US 7,361,334 B2
(45) Date of Patent: Apr. 22, 2008

(54) METHOD OF TREATMENT OF DIABETES THROUGH INDUCTION OF IMMUNOLOGICAL TOLERANCE

(76) Inventor: Paul P. Latta, 118 W. 4th Ct., Miami Beach, FL (US) 33139-5116

(*) Notice: Subject to any disclaimer, the term of this patent is extended or adjusted under 35 U.S.C. 154(b) by 421 days.

(21) Appl. No.: 10/823,263

(22) Filed: Apr. 13, 2004

(65) Prior Publication Data

US 2004/0191227 A1  Sep. 30, 2004

Related U.S. Application Data

(63) Continuation of application No. 10/660,924, filed on Sep. 12, 2003, which is a continuation of application No. 09/226,742, filed on Jan. 7, 1999, now abandoned, which is a continuation of application No. 09/049,757, filed on Mar. 27, 1998, now abandoned, which is a continuation of application No. 08/736,413, filed on Oct. 24, 1996, now abandoned.

(60) Provisional application No. 60/005,877, filed on Oct. 26, 1995.

(51) Int. Cl.
*A01N 63/00* (2006.01)
(52) U.S. Cl. ..................... 424/93.1; 424/93.7
(58) Field of Classification Search ............... 424/93.1, 424/93.7
See application file for complete search history.

(56) References Cited

U.S. PATENT DOCUMENTS

| | | | |
|---|---|---|---|
| 4,298,002 A | 11/1981 | Ronel et al. | |
| 4,353,888 A | 10/1982 | Sefton | |
| 4,378,016 A | 3/1983 | Loeb | |
| 4,673,566 A | 6/1987 | Goosen et al. | |
| 4,689,293 A | 8/1987 | Goosen et al. | |
| 4,696,286 A | 9/1987 | Cochrum | |
| 4,806,355 A | 2/1989 | Goosen et al. | |
| 4,892,538 A | 1/1990 | Aebischer et al. | |
| 4,902,295 A | 2/1990 | Walthall et al. | |
| 4,997,443 A | 3/1991 | Walthall et al. | |
| 5,182,111 A | 1/1993 | Aebischer et al. | |
| 5,262,055 A | 11/1993 | Bae et al. | |
| 5,290,684 A | 3/1994 | Kelly | |
| 5,425,764 A * | 6/1995 | Fournier et al. | 623/23.64 |
| 5,529,914 A * | 6/1996 | Hubbell et al. | 435/182 |
| 5,629,194 A * | 5/1997 | Dinsmore | 435/325 |
| 6,703,017 B1 * | 3/2004 | Peck et al. | 424/93.7 |

FOREIGN PATENT DOCUMENTS

| | | |
|---|---|---|
| CA | A1 2034641 | 5/1992 |
| EP | A2 0147939 | 7/1985 |
| EP | 0 536 807 A1 | 4/1987 |
| WO | WO 92/19195 | 12/1992 |
| WO | WO 95/03062 | 2/1995 |

OTHER PUBLICATIONS

Roep et al., Nature Reviews, 2004, v.4, pp. 989-997.*
Mestas et al., J. of Immunology, 2004, 172, pp. 2731-2738.*
Teuveson et al., Immun. Review 1993, N136, pp. 101-107.*
Feldman et al Transplant. Proc. 1998, 30, 4126-4127.*
Posselt et al Diabetes, 1992, v.41, pp. 771-775.*
Bingley, P.J. et al. (1994) "Combined analysis of autoantibodies, improves production of IDDM in islet cell antibody-positive relatives" Diabetes 43:1304(7).
Bonifacio, E. et al. (1995) "Islet autoantibody markers in IDDM: risk assessment strategies yielding high sensitivity" Diabetologia 38:816-822.
Christie, M.R. et al. (1994) "Antibodies is islet 37k antigen, but not to glutamate decarboxylase, discriminate rapid progression to IDDM in endocrine autoimmunity" Diabetes 43:1254(6).
Lee, H.C. et al. (1995) "Relationships among 64k autoantibodies, pancreatic beta-cell function, HLA-DR antigens and HLA-DQ genes in patients with insulin-dependent diabetes mellitus in Korea" Korean J. Intem Med. (Abstract only).
Tuomilehto, J. et al. (1994) "Antibodies to glutamic acid decarboxylase as predictors of insulin-dependent diabetes mellitus before clinical onset of disease" Lancet 343:1383-1385.
Zimmet, P.Z. et al. (1994) "Latent autoimmune diabetes mellitus in adults (LADA): the role of antibodies to glutamic acid decarboxylase in diagnosis and prediction of insulin dependency" Diabetic Medicine 11:299-303.
Zimmet, P.Z. et al. (1994) "Autoantibodies to glutamic acid decarboxylase and insulin in islet cell antibody positive presymptomatic type 1 diabetes mellitus: frequency and segregation by age and gender" Diabetic Medicine 11:868-871.
Atkinson M.A. et al. (1999) "The NOD mouse model of type 1 diabetes: as good as it gets?" Nature Medicine 5:601-604.

* cited by examiner

*Primary Examiner*—Michail Belyavskyi
(74) *Attorney, Agent, or Firm*—Knobbe Martens Olson & Bear LLP

(57) ABSTRACT

A method of creating tolerance to transplanted cells, tissue, or organs without the need for continuous immunosuppression. A tolerizing dose of a cell or tissue within a membrane structure is implanted into a patient. Once the patient becomes tolerant to the cell or tissue, a tissue or organ is implanted which will no longer be recognized as foreign matter. The method makes animal organs practical for human use, prevents autoimmune destruction as well as immune rejection. It has applications in treatment and prevention of many mammalian diseases.

13 Claims, 5 Drawing Sheets

METHOD OF TREATMENT OF DIABETES THROUGH INDUCTION OF IMMUNOLOGICAL TOLERANCE

RELATED APPLICATIONS

This application is a continuation of application Ser. No. 10/660,924 filed Sep. 12, 2003 which is a continuation of application Ser. No. 09/226,742 filed Jan. 7, 1999 now abandoned which was a continuation of application Ser. No. 09/049,757 filed Mar. 27, 1998 now abandoned, which was a continuation of application Ser. No. 08/736,413 filed on Oct. 24, 1996 now abandoned, which claims the benefit of priority under 35 U.S.C. 119(e.) of Provisional Application No. 60/005,877 filed Oct. 26, 1995.

FIELD OF THE INVENTION

The present invention relates to the induction of immunological tolerance to foreign cells, tissues and organs. More specifically, the invention relates to implantation of a tolerizing dose of cells or tissues encapsulated in a membrane in a mammal to establish immunological tolerance thereto.

BACKGROUND OF THE INVENTION

For some human diseases, including heart and liver failure, organ transplantation is the only alternative to certain death. While there were only 4,843 organ donors in the U.S. in 1993, there were 2,866 heart and 3,040 liver failure patients on the waiting list for these organs (*UNOS Update*, 10(2), 1994). Thus, because of timing and tissue matching problems, many patients die each year for lack of an available organ. For those lucky enough to receive an organ, the results are still less than ideal. The transplant procedure constitutes major surgery which is associated with attendant risks and is exceedingly expensive. After the surgery, the patient must be placed on a regimen of immunosuppressive drugs to keep the immune system from destroying the transplanted organ. As a consequence, the patient's entire immune system is suppressed for the rest of his life, significantly lowering his defenses against other serious disease threats such as infections, viruses or cancers.

For other diseases including kidney failure, pancreas failure and cystic fibrosis, transplantation has a lower mortality and morbidity rate than any alternative therapy. Even with its attendant problems of organ scarcity, surgical risk, high cost and permanent immunosuppression, for some of these cases it is still a more practical therapy than any alternative. The physician's choice in these cases is dependent on many variables including age, general health, severity of the condition, availability of organs and other factors. In 1994, there were 25,033 patients on the waiting list for human kidneys, 181 for pancreases and 1,250 for lungs (*UNOS Update*, 10:2, 1994).

For still other diseases, transplantation is known to be effective, although its attendant problems preclude its practical therapeutic use. This is true for many of the kidney, pancreas and lung patients described above. It is also true where whole pancreas transplantation can cure diabetes or liver transplantation can cure hemophilia but the risks outweigh the rewards.

Recently, for certain disease states; tissue transplants, as opposed to whole organ transplants, have been shown to be therapeutic in animals and even in man (Scharp et al., *Transplantation*, 51:76-85, 1991). Tissue transplantation requires full immunosuppression and carries the same risks and problems as already discussed for whole organ immunosuppression. The following treatments address the rejection of the transplanted tissue.

One implantation method involves pre-inoculation in the thymus with a small dose of cells, full temporary immunosuppression, then a full therapeutic dose at another site (Posselt et al., *Annals of Surgery*, 214:363-373, 1991). First, this has only been shown to work in rodents to date. No large animal or human test has been successful. Second, the human adult thymus is shrunken and may not be practical to treat with an adequate pre-dose. Third, the immunosuppression step, while temporary, does subject the patient to risks for that period of time. Fourth, it is not known whether a fully therapeutic dose will be tolerated, (i.e. not rejected) in humans. Fifth, this procedure may not protect against autoimmune destruction even if it does prevent rejection.

Another method of preventing rejection is irradiation of the recipient's bone marrow immune cells, implantation of bone marrow cells from the donor, then implantation of a full therapeutic dose of tissue or organ from the same donor (Illstad et al., *J. Exp. Med.*, 174:467-478, 1991). First, this has not been shown to work for tissue transplants in humans. Second, irradiation of immune cells, either partial or whole body, carries serious risks. Third, it is not known if the immune system will adequately protect from other threats. Fourth, it is not known if the method will protect from both rejection and autoimmune destruction in those disease states.

A further method of treatment to prevent rejection is by using monoclonal antibodies to suppress certain parts of the immune system (Andersson et al., *J. Autoimmun.*, 4:733-742, 1991). These tests have only been performed in rodents so it is not known if they would succeed in humans. Also, it is not known if the proper monoclonal antibody could be identified and created for each different disease state. In addition, the overall affect of these agents on the human immune system is not known.

Still another method of preventing rejection is encapsulation of the transplanted tissue in a semi-permeable membrane device which allows oxygen, nutrients and other small molecules to pass but prevents entry of large immune system cells (Lacy et al., *Science*, 254:1782-1784, 1991; Sullivan et al., *Science*, 252:718-721, 1991). There are several unresolved problems associated with this method. First, none of these devices has been shown to protect a therapeutic transplant in humans. To be suitable for human use, the material must be biocompatible; it must be sufficiently strong to last a long time when implanted; its porosity must be exactly correct to allow survival and function of the enclosed cells while keeping out cells and perhaps antibodies of the immune system; and finally, the device itself must be large enough to contain enough cells for a fully therapeutic implant and yet small enough to allow for some reasonable method of implantation which causes no damage to other internal organs.

To date, there has been very little effort to use transplantation as a potential prevention of disease due to all of the problems associated with transplantation as previously described. In addition, it is not yet known where transplantation can actually prevent a disease from occurring other than the obvious case of whole organ failures. Moreover, for many disease states, it is not known who will be afflicted. There is some evidence that interventional transplantation can have some preventive effect in rodents (Miller et al., *J. Neurol. Immunol.*, 46:73-82, 1993; van Vollenhoven et al., *Cell. Immunol.*, 115:146-155, 1988). Thus, a major role for preventive transplantation has not been investigated.

SUMMARY OF THE INVENTION

One embodiment of the invention is a method of creating immunological tolerance to foreign cells, tissues or organs in a mammal, comprising the step of implanting in the mammal a tolerizing dose of foreign cells or tissue encapsulated in a biologically compatible permselective membrane. The method may additionally comprise the step of administering to the mammal a curative dose of corresponding unencapsulated cells, tissue or organ. Advantageously, the mammal is a human, canine or feline. Preferably, the tolerizing cells are insulin-secreting cells; more preferably, they are pancreatic islet cells. According to one aspect of this embodiment, the membrane comprises polyethylene glycol. Preferably, the curative dose is between one and two orders of magnitude greater than the tolerizing dose. Advantageously, the tolerizing and curative doses are from the same species as the mammal. Alternatively, the tolerizing and curative doses are from a species different from the mammal. Preferably, the tolerizing and curative doses are porcine. The method may further comprise the step of administering one or more anti-inflammatory agents to the mammal prior to, at the same time as, or subsequent to administration of the curative dose. Preferably, the membrane has a molecular weight cutoff of about 150 kDa or less. Alternatively, the membrane has a pore size of about 0.4 μm or less. The membrane may also have a pore size of about 0.2 μm or less. Advantageously, when the tolerizing and curative doses are from a different species, the membrane has a molecular weight cutoff of about 150 kDa or less. Preferably, the tolerizing step is subcapsular, subcutaneous, intraperitoneal or intraportal and the curative step is intraperitoneal, intraportal or subcutaneous. The tolerizing dose may also be administered incrementally.

The present invention also provides a method of treating diabetes in a mammal in need thereof, comprising the steps of:

implanting in the mammal a tolerizing dose of foreign insulin-secreting cells encapsulated in a biologically compatible permselective membrane; then administering to the mammal a curative dose of corresponding unencapsulated insulin-secreting cells.

Preferably, the mammal is a human, canine or feline. Advantageously, the tolerizing dose is one to two orders of magnitude less than the curative dose. In another aspect of this preferred embodiment, the membrane comprises polyethylene glycol. Advantageously, the insulin-secreting cells are pancreatic islet cells. Preferably, the mammal and the insulin-secreting cells are from the same species. Alternatively, the mammal and the insulin-secreting cells are from different species. Preferably, the tolerizing and curative doses are porcine. The method may further comprise the step of administering one or more anti-inflammatory agents to the mammal prior to, at the same time as, or subsequent to administration of the curative dose. Advantageously, the membrane has a molecular weight cutoff of about 150 kDa or less. Alternatively, the membrane has a pore size of less than about 0.4 μm.

DETAILED DESCRIPTION OF THE PREFERRED EMBODIMENTS

Goals of the Invention

Figure 1:
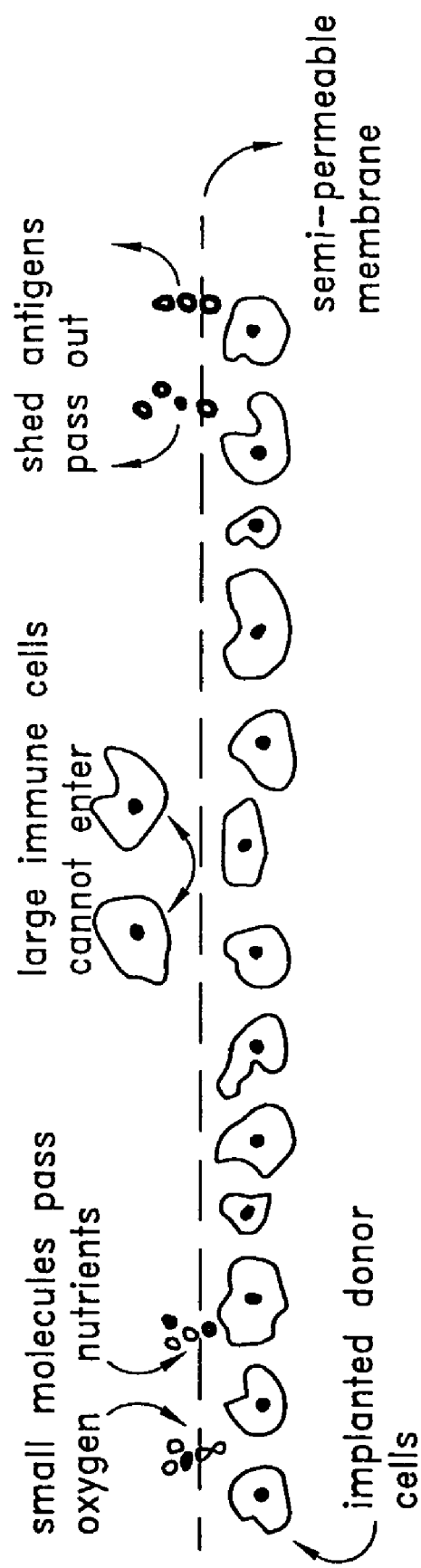
FIG. 1 is plane view illustrating the key properties of the membrane enclosing the cells. The membrane may be configured into many different device designs.

The problems discussed in the foregoing Background of the Invention have previously not been solved for either micro or macroencapsulation of cells in humans. The present invention overcomes these problems associated with transplantation. Thus, one goal of the invention is to eliminate the critical problems of transplantation in cases where whole organ transplantation is the only alternative to certain death. These are cases of heart or liver failure. The major advantage of the invention process for this application is that it eliminates the shortage of organs for the patients by making animal organs acceptable in humans. While there are only about 4,800 human organ donors in the U.S. each year, the supply of animal organs for transplant is not limited. The reason that animal organs are not presently used is that they are acutely rejected when transplanted into humans even with immunosuppression. Second, continuous immunosuppression is not required in the process of the invention, thus eliminating the risk of exposing the patient to other serious diseases while the immune system is suppressed. Third, the cost of organ transplantation is drastically reduced because of the unlimited supply of organs and because the continuous use of immunosuppressive drugs is not required.

A second goal of the invention is to make organ transplantation a safe, effective, practical therapy for those cases of disease where it is known now to be therapeutic but the risks associated with it prevent its widespread therapeutic use. Examples of these disease cases are kidney failure, pancreas failure and cystic fibrosis (lung failure). In these cases the advantages of the process of the invention eliminate the major obstacles. First, by making animal organs tolerated in humans the, shortage of organs for these transplant needs is solved. Second, by eliminating the need for continuous immunosuppression, these patients are not exposed to other serious disease threats without a fully functioning immune system. Third, because of plentiful organs and no continuous immunosuppression, the cost of this transplant procedure would be greatly reduced.

A third goal of the invention is to make cell or tissue transplants, as opposed to whole organ transplants, a practical therapy in cases where cells or tissue alone can cure a disease state by providing a lacking or deficient protein, enzyme or peptide. Examples of these cases are insulin-secreting islet cells for Type I diabetes, Factor VIII-secreting hepatic cells for hemophilia, dopamine-secreting adrenal chromaffin cells for Parkinson's disease and collagen for arthritis. A significant advantage of the process of the invention for these cases is that animal tissue or genetically engineered tissue expressing an absent or deficient protein of interest can be used if human tissue is scarce. In addition, cell types other than the normal protein-secreting cells can be engineered to secrete the protein of interest. For example, myoblasts can be engineered by standard methods to secrete insulin. The use of such cells is also within the scope of the present invention. Continuous immunosuppression is not needed to protect the transplanted tissue and the costs would be reduced. Thus, even if pre-inoculation into the thymus with immunosuppression or irradiation of bone marrow with immunosuppression or monoclonal antibodies could be identified and produced for many disease states or encapsulation of fully therapeutic doses of tissue in some membrane device can overcome many technical problems, the process of the invention is a safer and more practical therapy than any of these.

A fourth goal of the invention is the treatment of autoimmune diseases including diabetes, Alzheimer's, arthritis, multiple sclerosis, myasthenia gravis and systemic lupus erythematosus. In these diseases, the body's immune system attacks and destroys one's own tissue. By using the process of the invention, the immune system can be induced to accept grafted tissue or organs to replace those that have been destroyed without the autoimmune destruction of the newly transplanted graft. The advantage of this process is that organ rejection and autoimmune destruction are two completely different phenomena so that even with systems that may prevent rejection, in autoimmune diseases the grafts may still be destroyed by a different means. The process of the invention addresses both problems.

A fifth goal of the invention is to make transplantation a practical therapy to prevent certain diseases from ever occurring, as well as treating existing diseases as previously discussed. The advantage of the process that makes this possible is the immunomodulation effect which stops or prevents the immune system from destruction of self tissue. Thus, for all autoimmune disorders, the process can be used to intervene in the course of the disease at a critical point before the immune system is initiated into self-destruction of tissue that is necessary for normal body function.

As will be apparent from the ensuing detailed description of the invention, the present invention meets all of these goals. Additionally, the present invention also provides a number of advantages which would not have been readily apparent to one having ordinary skill in the art.

Overview

The present invention is a two step process. In the first step, a small number of cells or tissue is implanted into a mammal inside a device made of a biocompatible "permselective" membrane which protects the implanted cells from the mammal's immune system while at the same time allowing the cells to survive. A permselective membrane is one having a pore size selected so that it is small enough to prevent the entry of immunological factors such as cells or antibodies, yet large enough to allow the free passage of oxygen, nutrients and other molecules needed to sustain the transplanted cells. In addition, the membrane pores must allow the passage of antigens which are shed from the transplanted cells and prevent the entry of large immune system cells and antibodies. In a preferred embodiment, the mammal is a human. Alternatively, the mammal is a canine or feline.

One of ordinary skill in the art can readily determine the proper pore size for the permselective membrane for any particular application of the present invention. It is preferable to use the largest pore size possible to prevent the entry of the undesirable elements because the larger pores allow better diffusion of the desirable elements such as nutrients and oxygen across the membrane. Smaller pore sizes (e.g. those excluding molecules greater than 100,000 daltons) are not necessarily a problem for diffusion as has been shown in long-term survival of cells in a 50,000 dalton membrane in vivo implant (Lacy et al., Science 254:1782-1784, 1991).

Antigens shed from the transplanted cells pass through the permselective membrane into the body of the recipient where they are fully exposed to the immune system. The immune system will recognize these antigens as "foreign" and destroy them. This process will continue for some time with the immune system constantly destroying the shed antigens but not able to destroy the source which is the cells protected in the encapsulation device. In time, the immune system will begin to become tolerant of these antigens because they do no actual damage in the body and the constant source cannot be destroyed. At this time, the immune system is tolerant to that particular cell type from that particular donor.

Next, the second stage of the process is enacted. Now a fully therapeutic (curative) dose of cells, tissue or whole organ from the same donor as the tolerizing dose is implanted in the recipient for cure of the disease. Since this implant, whether cells, tissue or organ, is from the same donor as the small dose, it is recognized by the immune system as "self" and a rejection response is not elicited. The immune system is fully tolerant to the new implant. In one embodiment, the tolerizing dose is given as a single (bolus) dose. Alternatively, the tolerizing dose may be administered incrementally over several weeks or months. In a preferred embodiment, the incremental tolerizing dose is the same as the bolus dose, only spread out in even increments. In another embodiment, the total incremental tolerizing dose is one to three times the bolus tolerizing dose. As for the bolus tolerizing dose, the incremental tolerizing dose is typically one to two orders of magnitude lower than the curative dose.

In addition to eliminating continuous immunosuppression, this process makes animal organs and cells available for human implants (xenografts). Presently, these organs or tissues are acutely rejected in humans because of the wide immunological barriers between the species. With the process of the invention, even animal tissue will be tolerated because tolerance is induced gradually over time. The availability of animal organs for human use will save many thousands of lives each year which are now lost due to the shortage of available human organs for transplantation. In addition, this process will allow transplant therapy for autoimmune diseases such as diabetes, arthritis, myasthenia gravis and multiple sclerosis. This is possible because as the immune system is tolerized to the new tissue by the initial small implant, the self-destructive autoimmune process is suppressed. So, for diseases requiring organs or cellular transplants, this process eliminates current shortages by making unlimited supplies of animal organs and cells available, eliminates the need for continuous immunosuppression, and protects the transplants from both rejection and autoimmune destruction. One particularly preferred source of xenograft cells or tissue for both the tolerization and curative steps is porcine cells or tissue.

Even with the tolerizing effect of the xenograft, because of the wide species differences, an initial inflammatory reaction may occur in response to the curative dose. Thus, in one embodiment of the invention, the xenograft recipient is administered one or more anti-inflammatory agents. The anti-inflammatory agent is administered either systemically or locally at the implantation site. The agent may be administered prior to the implant, at the time of implantation or subsequent to the implant for a time necessary to overcome the initial inflammatory reaction. The agents may be over-the-counter preparations such as acetaminophen or ibuprofen, or a specific immunosuppressive agent such as Cyclosporine (Sandoz) or Imuran (azathioprine, Burroughs-Wellcome). The agent may also block the binding of a particular antigen such as CTLA4Ig (Bristol Myers Squibb). The amount of anti-inflammatory agent to be administered is typically between about 1 mg/kg and about 10 mg/kg. The extent of inflammation will determine whether the administration of such an agent(s) is necessary. The need for such agents is only temporary and not required for the ongoing survival and function of the transplant.

The process of the invention can also be used to prevent certain diseases, particularly autoimmune disorders. In these cases the process is as follows. First, patients at high risk for the disease or already in the very early phase of the disease are identified. At the critical time of the onset, the process is intervened with the small encapsulated tissue. For example, islets are used for Type I diabetes and collagen is used for arthritis. This implant of foreign tissue immediately diverts the attention of the immune system to the new foreign invader and it begins the process to destroy this new threat. Because of this diversion, the process of self-destruction of desirable tissue that was just beginning is suppressed, then abandoned, then forgotten. It is, in essence, "switched off" and the damage is prevented.

Implantation of Cells to Treat Existing Diseases

The first step of this method involves acquiring small amounts of cellular tissue for the initial tolerizing implant. The method in which tissue is obtained depends on the type of tissue needed, the source of the tissue, the donor, and the amount of tissue needed. These methods are generally well known by those skilled in the art of tissue digestion, separation, purification, culture, and the like. The following examples are only used to illustrate that these methods are readily available.

Islet Cells for Treatment of Diabetes

Islets are small clusters of cells located in the pancreas of mammals. They are composed of alpha cells which make and secrete somatostatin, beta cells which make insulin, delta cells which make glucagon and other cells which make other proteins. To isolate the islet cells which make up only 1-2% of the pancreas from the surrounding acinar tissue, the digestive enzyme collagenase is used. This process is described by Ricordi (*Diabetes* 37:413-410, 1988, hereby incorporated by reference). Once the islets are obtained, they are purified from acinar cells and can then be implanted fresh, cultured for extended periods, cryopreserved indefinitely or encapsulated.

For use in human treatments, primary islet cells are obtained from human cadaver donors or from suitable mammalian sources such as rat, cow, or pig. For use of animal tissue in humans, it is desirable to assure safety of the animal source by using specific pathogen-free (SPF) or gnotobiotic colonies or herds of animals. As an alternative to a primary cell source, an engineered cell line which is genetically altered to produce the proper regulated amounts of insulin, glucagon, somatostatin, etc. is also suitable for treatment of diabetes.

Adrenal Chromaffin Cells for Parkinson's Disease, Alzheimer's and Huntington's Disease Adrenal chromaffin cells have multiple applications. They secrete the neurotransmitter dopamine for amelioration of Parkinson's disease, fibroblast growth factor, and can be engineered to secrete nerve growth factor which will counter degeneration and cell death in Alzheimer's and Huntington's disease. A collagenase digestion method of isolating adrenal chromaffin cells from the adrenal gland is described by Livett (*Physiol. Rev.* 64:1103-1161, 1984). Human or other mammalian sources can be appropriate sources of this tissue.

Moreover, mammalian cells can also be genetically engineered to secrete certain proteins or peptides whose absence or deficiency is the cause of various genetic diseases (i.e. adenosine deaminase deficiency). In addition, such cells can also be engineered to secrete various cytokines and growth factors for the treatment of viral infections (i.e., interferon-γ) and cancer (i.e., interleukin-2). Hormone deficiencies can also be treated by this method. Mammalian cells are transfected with an expression vector containing a gene encoding such a therapeutic protein or peptide. These expression vectors are constructed using standard methods well known to one of ordinary skill in the art. A tolerizing dose of these cells is encapsulated as described herein and implanted into a mammal. Two to three weeks later, a curative dose of the same cells is implanted into the mammal. The cells are no longer recognized as foreign, are not destroyed by the host immune system and continue to secrete the desired therapeutic protein.

Other conditions treatable by encapsulated cells producing peptides, proteins or other therapeutic agents include hypoparathyroidism (thyroid hormone), hyperadrenocorticalism (adrenocorticotrophic factor), dwarfism (growth hormone), Gaucher's disease (glucocerebrosidase), Tay-Sachs (hexosaminidase A) and cystic fibrosis (cystic fibrosis transmembrane regulator). In addition, cells expressing stimulatory or inhibitory cytokines can be encapsulated, resulting in stimulation or inhibition, respectively, of a particular cell type. For example, erythropoietin stimulates red blood cell production, interleukin-2 stimulates the proliferation of tumor-infiltrating lymphocytes and interferons inhibit certain types of tumor cells. Other conditions contemplated for treatment using the method of the present invention include amyotrophic lateral sclerosis, Alzheimer's disease, Huntington's Chorea, epilepsy, hepatitis, anxiety, stress, pain, addiction, obesity, menopause, endometriosis, osteoporosis, hypercholesterolemia, hypertension and allergies.

Other Cell Sources and Methods for Other Diseases

Other cell/tissue sources and methods include collagen recovery from chicken for prevention and treatment of arthritis, Schwann cells from myelin tissue for prevention and treatment of neural degeneration and Factor VIII from liver hepatocytes for treatment and prevention of hemophilia.

The amount of cells or tissue necessary for the initial tolerizing implant will vary depending on the disease, site, source, whether the tissue is primary or immortalized and other factors. Generally, the tolerizing dose is one or two orders of magnitude less than a full dose implant. For example, in diabetes it usually takes between about 10,000-20,000 islets/kg of body weight to provide adequate insulin production for normoglycemia. Accordingly, the initial implant dose for tolerization is about 100-2,000 islets/kilogram of body weight. Although the size of these doses are not known for all disease states, they can be optimized using routine dose/response experiments well known to one of ordinary skill in the art. In general, between about 100 cells/kg body weight and about 5,000 cells/kg body weight are suitable for tolerization. The corresponding curative doses are between about one and two orders of magnitude higher than these numbers.

Preparation of Encapsulation Device, Loading of Cells and Implantation

The membrane for the device is chosen for the application needed based on its biocompatability, permeability, strength, durability, ability to be manipulated and other important considerations. A number of materials have already been shown to be acceptable for implants in mammals. Examples of some of these materials are PAN/PVC acrylic co-polymers, hydrogels such as alginate or agarose, mixed esters cellulose, polytetrafluoroethylene (PTFE)/polypropylene (Lum et al., *Diabetes* 40:1511-1516, 1991; Aebischer et al., Exp. Neurol., 111:269-275, 1991; Liu et al., *Hum. Gene Ther.* 4:291-301, 1993; Hill. et al., *Cell Transplantation* 1:168, 1992, all hereby incorporated by reference) and polyethylene glycol (PEG) conformal coating configurations (U.S. Pat. No. 5,529,914, hereby incorporated by reference).

A critical factor is the pore size that can be produced in the material chosen. For example, PEG macromers can vary in molecular weight from 0.2-100 kDa. The degree of polymerization, and the size of the starting macromers, directly affect the porosity of the resulting membrane. Thus, the size of the macromers are selected according to the permeability needs of the membrane. It is believed that for xenograft transplants (animal to human), antibodies of the immune system and complement are involved in rejection (Bach et al. *Transplantation* Overview 6(6):937-947, 1991). In this case, a pore size (molecular weight cutoff) of 150 kDa or smaller is desired to prevent the passage of the smallest immune antibody (IgG) through the pores of the membrane capsule. Thus, the application and its conditions will determine the choice of membrane material from many available alternatives. Likewise, the configurations of the device will be determined by the application. For purposes of encapsulating cells and tissue in a manner which prevents the passage of antibodies across the membrane but allows passage of nutrients essential for cellular metabolism, the preferred starting macromer size is in the range of about 3 kDa to 10 kDa, with the most preferred being about 4 kDa. Smaller macromolecules result in polymer membranes of a higher density with smaller pores.

It is also believed that for allografts (human to human), only entry of immune system cells must be blocked to prevent rejection of transplanted tissue or organs (Auchincloss, Jr., *Transplantation* Overview 46(1):1-20, 1988. In addition, it is also desirable to exclude other cells, the smallest of which are red blood cells which have a size of about 7 μm. Accordingly, a membrane having a molecular weight cutoff of about 150 kDa is also suitable for encapsulation of allograft cells or tissue because such membranes will prevent entry of such cells. In an alternative embodiment, the pore size for allografts is about 0.4 μm or less to prevent the entry of immune and non-immune cells into the device. Cells can also extend processes ("arms") which can enter openings having a size of about 0.2 μm. Thus, in another preferred embodiment, the pore size is about 0.2 μm or less. In a most preferred embodiment, the pore size is as small as possible to exclude entry of detrimental components, but allows cell survival by permitting vital molecules such as nutrients, proteins and oxygen to freely pass through the permselective membrane. A desired pore size may be obtained by adjusting the crosslink density and length of PEG segments by one of ordinary skill in the art without undue experimentation.

If retrieval of the initial implant is unnecessary or undesirable, then a suitable configuration may be microcapsules where only a few or even single cells are each enclosed in separate membranes. Because of the small volume in this case, the microcapsules may simply be injected into one of many sites for the implant. If it is desirable to retrieve or reload the device or larger numbers of cells are necessary, a "macrocapsule" may be constructed wherein many cells are enclosed together inside one membrane. In this case, it has been shown that the environment inside the macrocapsule may need special conditions to allow the cells to survive. For example, an alginate matrix has been used to immobilize islet cells and prevent their aggregation and subsequent central necrosis (Lacy et al., *Science,* 254:1782-1784, 1991).

Figure 3:
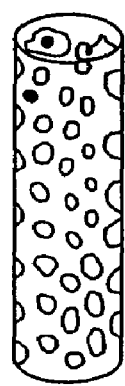
FIG. 3 is a tubular view of one design of the invention, wherein the membrane is cast or rolled into a tubular configuration. The cells are loaded in the lumen and the ends are sealed.
Figure 2:
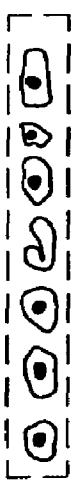
FIG. 2 is a plane view of one design of the invention, wherein two layers of the membrane are used in a flat sheet configuration where cells are "sandwiched" in between the two membranes and then the ends are sealed.

For other cell types a different environment may be needed. The macrocapsule may be of any shape that is practical. Examples of shapes commonly used by those skilled in the art are: 1) flat sheet "sandwiches" where two layers of the membrane are top and bottom on the cells and the ends are sealed by heat welding, gluing, or other known means (FIG. 2). This method provides a large surface area for membrane exposure to the host systems and generally short diffusion distances which helps transport substances across the membrane; 2) A tubular membrane formed by co-extrusion or rolling a flat sheet into a tube and sealing the ends (FIG. 3).

Figure 4:
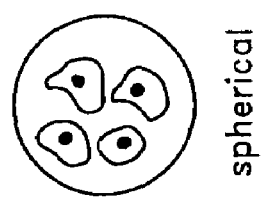
FIG. 4 is a spherical view of one design of the invention, wherein the membrane is cast in a spherical configuration and cells may be encased one in each device (microcapsule) or many in a device (macrocapsule).

The cells can be placed inside the lumen at the same time the membrane is formed if co-extrusion is employed. If the tube is made first, the cells are loaded by syringe or other means and the ends are sealed by heat welding, gluing or other known means. As previously discussed, various matrices may be employed as needed by the enclosed cells. The tubes can be any suitable length and may be joined at the ends (potted) or woven if multiple tubes are used; 3) a spherical shape (FIG. 4) which has a large surface area compared to its volume and is efficient in some applications.

These are only illustrative examples of how membranes may be configured into devices to hold cells. One of ordinary skill in the art will appreciate that many more configurations are possible, thus providing great flexibility for many conceivable applications.

The loaded devices are then implanted into patients in need of therapy. The method of implantation, site and duration are dependent on the disease being treated. For example, in diabetes it is desirable to have the shed antigens processed by the liver. Therefore, implantation in the peritoneum where the portal circulation would carry the antigens directly to the liver (intraportal) is a preferred site. Alternatively, if the dose is a small enough volume (i.e. 10 μl or less), direct injection into the portal vein is preferred. Other implantation sites include under the kidney capsule and subcutaneous implantation.

For Parkinson's disease, the cells should be processed first in the brain. Thus implanting into the interstitial region of the brain is a preferred site. For each site, the method of implantation may be different. For example, intraperitoneal placement of a device for diabetes may be performed by a minimally invasive laparoscopic procedure. To place a device in the brain, the neurosurgeon commonly uses stereotaxic instruments to ensure exact placement. For a subcutaneous implant, a small incision to allow a trocar to be inserted may be used. For each preferred site, those skilled in the art will recognize the most efficient method of implantation.

Once implanted, the cells are left in place for a period of time during which tolerization will occur. This time period will vary depending on the disease treated, whether an allograft or a xenograft transplant is being used, site of the implant, and other factors. Generally, tolerization requires from a few weeks to a few months. During this time, the transplanted cells constantly shed antigens from their surface. These antigens comprise a variety of small molecules which are constantly being replaced by living cells The antigens can pass freely out of the pores of the membrane and into the recipient at the locations of the implant and eventually into the circulatory system. The immune system immediately recognizes these antigens as "foreign" and initiate its mechanisms to protect the recipient from the intruder. These mechanisms are complex and not completely understood. Generally, it is believed that if the foreign matter is from a closely related species (allogeneic), cells of the immune system play the primary role in the immunological response. These cells include T-cells, macrophages, neutrophils, and natural killer cells which seek out the source of the invasion and destroy the foreign matter. If the foreign matter is a transplanted xenogeneic organ, preformed antibodies cause hyperacute (within minutes) reaction and rejection of the organ. If the foreign matter is xenogeneic cells or tissue, the antigen may not be presented and the preformed antibodies may not be the primary mechanism of rejection. Instead, macrophages stimulate killer T-lymphocytes and later (8-10 days) antibody stimulation causes final rejection of cells or tissue.

In the present invention, however, neither system can destroy the cells of the implant when the pore size of the membrane is properly selected for the application. For example, if allografts are destroyed by immune cells, then the membrane pores must only prevent entry of these cells and thus may be about 0.4 µm or smaller. Likewise, if it is necessary to prevent antibodies from reaching the cells, the pores must be smaller than the smallest of the human antibodies, IgG, which is 150 kDa Of course, a pore size having a molecular weight cutoff of about 150 kDa or less is suitable for tolerization in both allografts and xenografts.

The use of a permselective membrane prevents the immune system from destroying cells encapsulated therein, even though the immune system recognizes the implant tissue as foreign and mounts a classical response. The immune response cannot destroy the cells because they are protected within the membrane device. Because the immune system cannot destroy the cells even over time, the system will come to tolerate the implant and cease trying to destroy it. While the mechanism for this tolerization is not known, it is analogous to desensitizing patients to allergic immune reactions (i.e. antibiotics or bee stings). In fact, an alternative method to the single tolerizing implant is the addition of more cells with more implants over time if necessary. At this point, the immune system basically recognizes this cellular material as "self" and no longer mounts an immune response against it.

Implantation of Full Curative Dose

When the patient has been tolerized to the cells of the implant, a full curative curative size dose of the tissue or whole organ is administered as described in the following examples.

Whole Organ Transplants—Allografts

In one embodiment, the method is used for a human allograft. In this embodiment, the tissue for the initial implant is taken from a living related kidney donor by biopsy or similar method and a tolerizing dose is implanted into the patient. When the patient is tolerized, the whole kidney is taken from the donor and transplanted into the recipient. The graft is accepted with no continuous immunosuppression being necessary.

Whole Organ Transplants—Xenografts

For most embodiments, it is preferable to use animal organs for human transplants. In these embodiments, the procedure is as follows: suitable animal donors are identified. Sources of these donors may be genetically identical (inbred). Tolerizing cells are taken from any animal in the colony. Later, the whole organ is taken from any other animal in the colony. It is preferable that these sources are free of all contaminants of risk to humans so they would preferably be specific pathogens free (SPF) or gnotobiotic (totally isolated in sterile conditions) colonies or herds. Heart, lungs, livers, kidneys, pancreases and other organs may be used in this embodiment, thus eliminating the critical shortage of these organs from the limited number of available human organ donors.

Cellular Transplants—Allografts

In this embodiment, the method is used for human to human cellular transplants. A full size therapeutic dose is obtained from the cadaver donor source as previously described. For example, islet cells are obtained from the pancreas of a human donor. The small amount needed for the tolerizing implant is taken from the preparation, encapsulated and implanted as previously described. The remainder of the cells are cryopreserved by known methods (Kneteman et al, *Transplant. Proc.* 18:182-185, 1986) and are held until tolerization is completed. The full preparation is then thawed and ready for implantation. If, in this embodiment, it is necessary to acquire cells from more than one donor to have enough for a curative implant, then the cells for the initial implant are taken from multiple donors and mixed for the implant. The recipient is therefore tolerized to all of the cells from the multiple donors.

Cellular Transplants—Xenografts

As with whole organs, the present method allows the use of cellular transplants from animals as well. Cells for the initial implant are taken from genetically identical animals or multiple pooled animals as previously described. When the individual is ready for the full transplant, cells may be taken from any other member of the genetically identical colony or from multiple pooled animals if necessary for sufficient curative quantities.

The implantation procedure for the fully curative dose of cells, whether allograft or xenograft, is dependent on the disease, the quantity of cells, the site, and other factors. For example, for diabetes, a preferred procedure for the implantation of islet cells in humans is to inject the cells through the portal vein so that they become lodged in lobes of the liver. This procedure is done under local anesthesia and is minimally invasive to the patient. For treatment of neural disorders, cells can be implanted into any selected area of the brain by well known stereotaxic surgical procedures. Those skilled in the art will know preferred methods for cellular implantation for each embodiment.

Implants for Prevention of Diseases

Identification of patient populations is dependent on the ability to diagnose patients at high risk of developing certain diseases or those in early stages of the disease. Rapid progress has been made in this area of medicine primarily due to major advances in understanding and mapping the human genome. In addition, DNA amplification methods, notably the polymerase chain reaction (PCR), can be used to diagnose certain genetic disorders. Other research areas for predicting diseases are advancing as well.

In diabetes, the use of immune marker autoantibodies to establish preclinical diabetes has been well studied (Palmer, Diabetes Rev. 1(1):104-116, 1993). When these patients are identified, the physician determines at what point in the course of the disease it would be most advantageous to intervene.

Individuals determined to be at risk for development of a particular disease are implanted with the appropriate cell type as described above. Methods for acquiring small amount of cellular tissue for the initial tolerizing implant, tissue types, the amount of tissue necessary for implantation, preparation of the encapsulation device, loading cells into the device, implanting the device into a patient, membrane parameters, device configuration, implantation methods, curative dose administration, etc. are the same as discussed hereinabove for disease treatment.

Treatment of Diseases Arising from Lack of a Hormone

A study was performed using an insulin-producing mouse tumor cell line encapsulated in a permselective membrane coating as described in the following example.

EXAMPLE 1

Implantation of Mouse Insulinoma Cells

The NIT insulin-producing mouse tumor cell line was encapsulated with PEG conformal coatings of a single, configuration, 11% PEG 4,000 kDa molecular weight (See U.S. Pat. No. 5,529,914), which corresponds to a molecular weight cutoff of between about 10 kDa and about 70 kDa. The encapsulated cells were implanted beneath the kidney capsule at two different doses into C57B6 mice of a different allograft haplotype in which diabetes had been induced by intravenous injection (tail vein) of 167 mg/kg body weight of streptozotocin (Upjohn, Kalamazoo, Mich.). Induction of diabetes by streptozotocin injection is a well known procedure which destroys pancreatic insulin-producing β cells.

Figure 5:
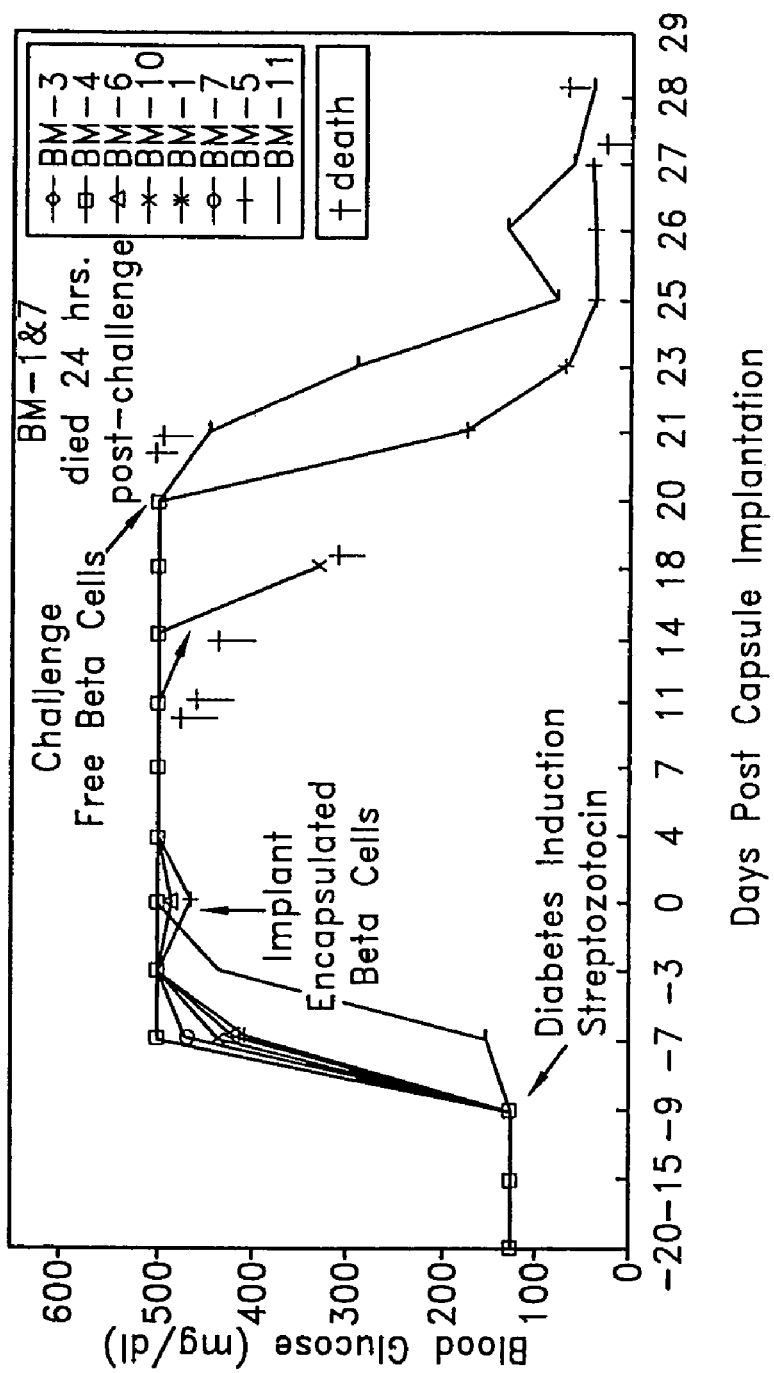
FIG. 5 is a graph showing blood glucose levels in mice implanted with a tolerizing dose of 100 encapsulated NIT insulinoma aggregates.
Figure 6:
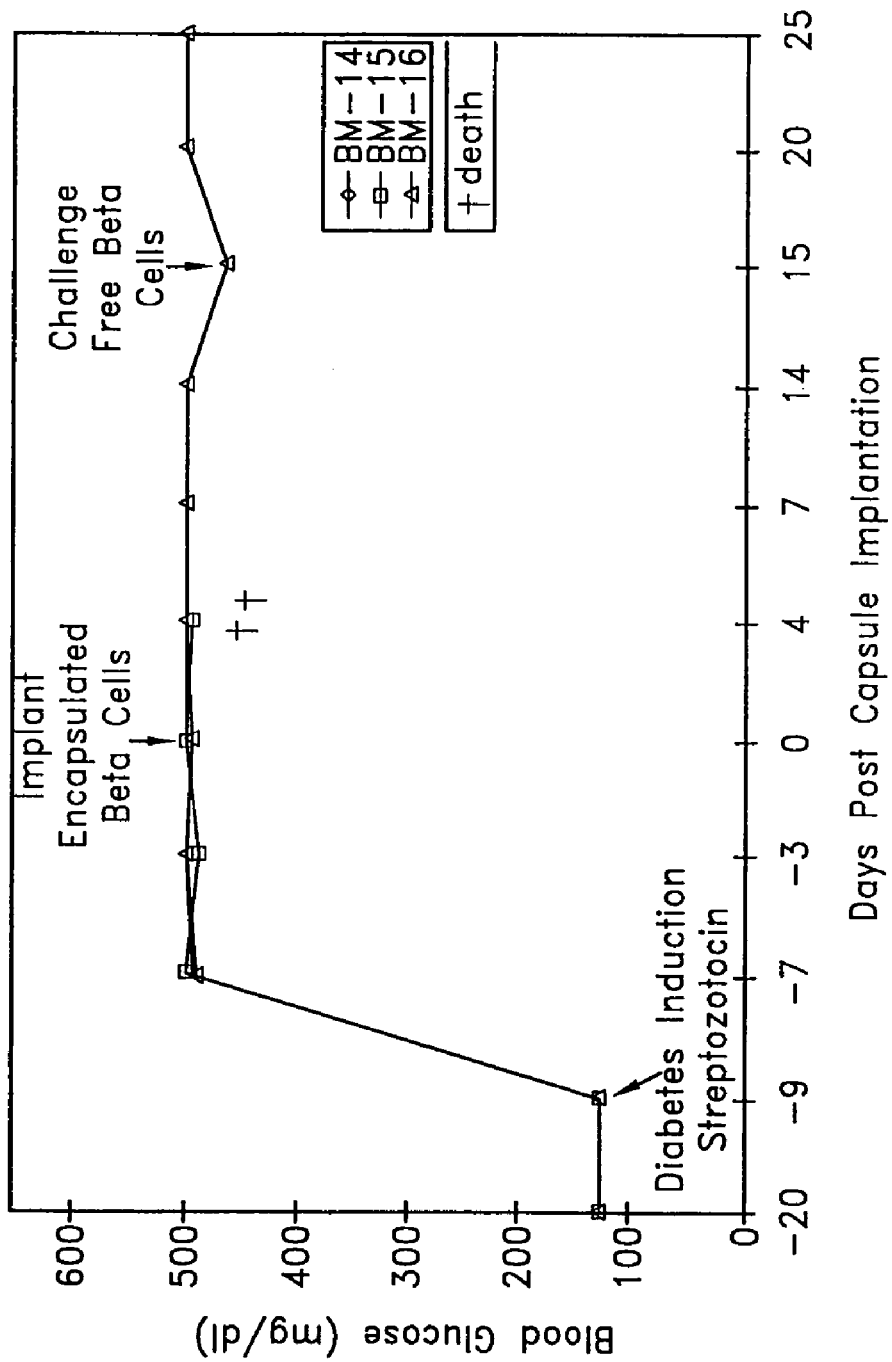
FIG. 6 is a graph showing blood glucose levels in mice implanted with a tolerizing dose of 50 encapsulated NIT insulinoma aggregates.
Figure 7:
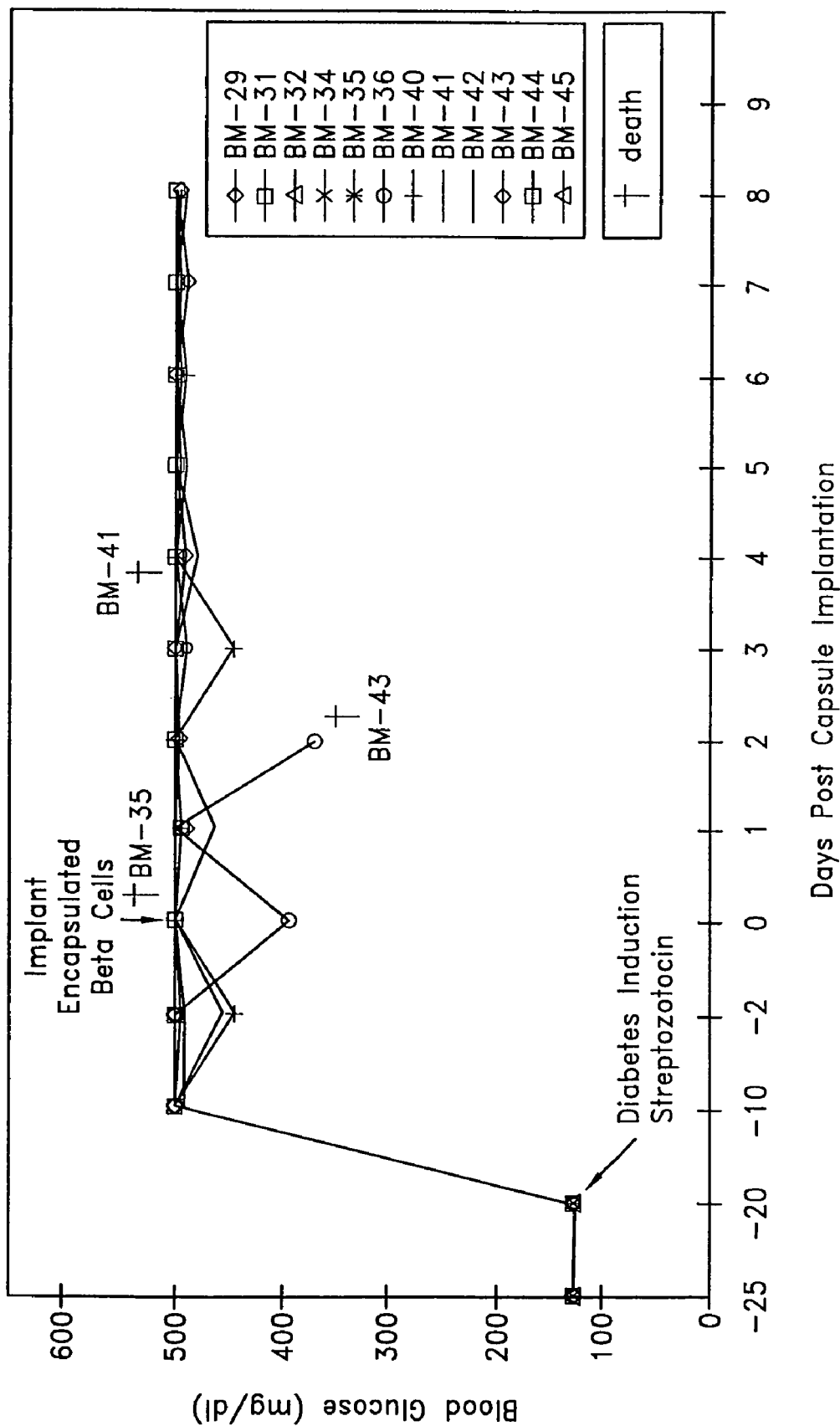
FIG. 7 is a graph showing blood glucose levels in non-tolerized control mice.

Tolerizing doses of encapsulated insulinoma cells were 50 or 100 cell aggregates, each containing about 1,000 cells. Encapsulated cells were implanted beneath the kidney capsule using standard surgical procedures. Curative implants of unencapsulated insulinoma cells (2,000-3,000 insulinoma cell aggregates, each containing about 1,000 cells) were administered by free intraperitoneal injection 15 or 20 days after the tolerizing dose to determine whether a sufficient quantity of cells survived. Control animals were given only the curative dose of insulinoma cells. Blood glucose levels were monitored and are shown for the 100 encapsulated NIT aggregate tolerizing dose, 50 encapsulated NIT aggregate tolerizing dose and non-tolerized controls (FIGS. 5, 6 and 7, respectively).

The severity of streptozotocin-induced diabetes in these mice caused several of the animals to die during the periods of observation and during procedures done as part of the study. Table 1 indicates the number of animals involved in the study and their outcomes. The degree of diabetes is very high, with values over 500 mg/dl (shown as 500) for all streptozotocin-induced animals in the study. Many of these severely diabetic animals died of their diabetes during the study or following a procedure as noted. As shown in FIG. 5, of the first group of 8 diabetic mice receiving 100 encapsulated aggregates, only four survived for the challenge 20 days later with the unencapsulated aggregates. Two of these died overnight following the IP injection. The remaining two recipients both had a sudden and marked reduction in their glucose values between 5 and 9 days, with glucose values reaching levels of 40 mg/dl and below (BM5 and BM11, FIG. 5 and Table 1). If the insulin-secreting insulinoma cells induce immunological tolerance, the curative implant will be recognized as "self" and will not be destroyed by the recipient's immune system. Because the NIT cells are tumor cells which double every 2-3 days in vitro, their survival would be expected to result in recipient hypoglycemia due to the increasing insulin-producing cell mass that would occur from living and growing tumor cells.

In the second group of three recipients of 50 encapsulated aggregates for 15 days, two died of their diabetes prior to challenge with unencapsulated NIT cells. The one animal that received the challenge of unencapsulated NIT cells (BM16) has not exhibited any reduction in blood glucose values for the same time of observation (FIG. 6). None of the control animals only challenged with unencapsulated NIT cells exhibited any reduction in blood glucose values (FIG. 7).

The results indicate that encapsulated NIT cells given as a small mass prior to a large, unencapsulated curative cell implant permits the second curative dose to survive, reducing blood glucose values in a pattern suggestive of NIT tumor cell growth. A smaller dose of encapsulated NIT cells did not give this result. Control animals that only received unencapsulated NIT cells in a curative dose exhibited no reduction in blood glucose. These results indicate that the preliminary encapsulated implant tolerized the host to the following unencapsulated curative dose. When such a preliminary encapsulated implant was not done, the curative unencapsulated implants had no effect on blood glucose and were presumably destroyed by the host.

TABLE 1

| Animal # | Toler. Encap. Implant | # Encap. Cell Agg. Tol. Dose | Delay to Cure Implant | Unencap. Cell Implant | # Unenc. Cell Agg. Cure | Effect on Blood Glucose |
|---|---|---|---|---|---|---|
| BM1 | yes | 100 | 20 days | yes | 2348 | none-died* |
| BM3 | yes | 100 | 20 days | no-died | — | n/a |
| BM4 | yes | 100 | 19 days | no-died | — | n/a |
| BM5 | yes | 100 | 20 days | yes | 2348 | down to 40 |
| BM6 | yes | 100 | 20 days | no-died | — | n/a |
| BM7 | yes | 100 | 20 days | yes | 2348 | none-died* |
| BM10 | yes | 100 | 20 days | no-died | — | n/a |
| BM11 | yes | 100 | 19 days | yes | 2348 | down to 40 |
| BM14 | yes | 50 | 15 days | no-died | — | n/a |
| BM15 | yes | 50 | 15 days | no-died | — | n/a |
| BM16 | yes | 50 | 15 days | yes | 2348 | none-500 |
| BM29 | no | 0 | — | yes | 2352 | none-500 |
| BM31 | no | 0 | — | yes | 2352 | none-500 |
| BM32 | no | 0 | — | yes | 2352 | none-500 |
| BM34 | no | 0 | — | yes | 2352 | none-500 |
| BM35 | no | 0 | — | yes | 2352 | none-died* |
| BM36 | no | 0 | — | yes | 2352 | none-500 |
| BM40 | no | 0 | — | yes | 2352 | none-500 |
| BM41 | no | 0 | — | yes | 2352 | none-died* |
| BM42 | no | 0 | — | yes | 2352 | none-500 |
| BM43 | no | 0 | — | yes | 2352 | none-died* |

TABLE 1-continued

| Animal # | Toler. Encap. Implant | # Encap. Cell Agg. Tol. Dose | Delay to Cure Implant | Un-encap. Cell Implant | # Unenc. Cell Agg. Cure | Effect on Blood Glucose |
|---|---|---|---|---|---|---|
| BM44 | no | 0 | — | yes | 2352 | none-500 |
| BM45 | no | 0 | — | yes | 2352 | none-500 |

*Died during course of experiment-no effect on blood glucose

EXAMPLE 2

Use of Encapsulated Islets for Induction of Allograft Tolerance in Rats

Rat pancreatic islet cells are isolated by a standard collagenase digestion method (Ricordi, *Diabetes* 37:413-410, 1988) and cultured for three days prior to PEG encapsulation. Donor islets are derived from the Wistar Furth (WF) strain having MHC haplotype RT1-U. Recipients are of the Lewis strain having MHC haplotype RT1-1. Transplants across this strain combination are normally rejected within three weeks. Islet transplant mass is dosed on the basis of a standard 150 μm diameter rat islet; an Islet Equivalent (Ieq). Islets are quantified and tested for sterility and mycoplasma prior to encapsulation and implantation.

Islet cells are conformally coated with 11% PEG 4,000 kDa molecular weight by the method described in U.S. Pat. No. 5,529,914. As a negative control, acellular cross-linked dextran beads are encapsulated in a similar manner. Diabetes is induced in fasted Lewis rats by intravenous injection of streptozotocin (65 mg/kg) one week prior to implantation of the tolerizing dose and monitored during that week for blood glucose levels and weight changes. Rats are considered diabetic once their blood glucose level exceeds 350 mg/dl. Rats having a minimal weight loss and blood glucose levels of 300-350 mg/dl are used for the study.

Diabetic rats are implanted by trochar with a subcutaneous 30 day time release depot insulin (Linplant, Lishin, Ontario, Canada) to reduce the chances of ketosis/acidosis and to stabilize their diabetes. Animals remain hyperglycemic at this Linplant dose (2 units of bovine insulin in 24 hours—lasts 30 days).

Diabetic MHC disparate Lewis rats are surgically implanted once with encapsulated donor WF islets at the renal subcapsular site after anesthetization. The dose of implanted cells varies as outlined in Table 2.

TABLE 2

| Group | N | Dose | Rationale |
|---|---|---|---|
| 1 | 12 | 1200 encap islets | high dose sensitization/tolerization |
| 2 | 12 | 600 encap islets | low dose tolerization |
| 3 | 12 | 300 encap islets | very low dose tolerization |
| 4 | 12 | 1200 encap acellular beads | control for polymer |

As a control, a set of recipients (Group 4) is implanted with encapsulated acellular beads to control for possible polymer effects in tolerization. All implanted animals are maintained for intervals as shown in Table 3 prior to the second transplantation. At the time of implantation, serum samples from each animal are drawn and retained for future immunological analysis.

TABLE 3

| Group | N | Dose | Implant Interval (days) | Rationale |
|---|---|---|---|---|
| 1a | 4 | 1200 encap islets | 30 | high dose sensitize/tolerize-short interval |
| 1b | 4 | 1200 encap islets | 60 | high dose sensitize/tolerize-intermediate interval |
| 1c | 4 | 1200 encap islets | 90 | high dose sensitize/tolerize-long interval |
| 2a | 4 | 600 encap islets | 30 | low dose tolerization-short interval |
| 2b | 4 | 600 encap islets | 60 | low dose tolerization-intermediate interval |
| 2c | 4 | 600 encap islets | 90 | low dose tolerization-long interval |
| 3a | 4 | 300 encap islets | 30 | very low dose tolerization-short interval |
| 3b | 4 | 300 encap islets | 60 | very low dose tolerization-intermediate interval |
| 3c | 4 | 300 encap islets | 90 | very low dose tolerization-long interval |
| 4a | 4 | 1200 encap acell-beads | 30 | polymer control-short interval |
| 4b | 4 | 1200 encap acell-beads | 60 | polymer control-intermediate interval |
| 4c | 4 | 1200 encap acell-beads | 90 | polymer control-long interval |

During the indicated period, animals are monitored for weight changes and blood glucose levels. One week before the second transplant, one animal in each of Groups 1a-1c, 2a-2c, 3a-3c and 4a-4c is sacrificed and the implant site analyzed by histological methods for determining viability of the tolerizing cells.

Lewis rats remaining in Groups 1-4 receive a second transplant (curative dose) of WF islets which are unencapsulated. Transplant sites in each animal are intraportal (IP) at a dose of 6,000 Ieq and at one kidney with a dose of 100 Ieq (See Table 4). 6,000 Ieq implanted into the liver is known to be a curative dose in the rat diabetes model. The 100 Ieq kidney capsule implant is only for histology at the end of the experiment. At the time of the second implant, serum samples from each animal are drawn and retained for future immunological analysis. For the next three weeks, animals are monitored for blood glucose levels and weight changes. At the termination of the experiment, graft sites are processed for histology. At this time, serum samples from each animal are again drawn and retained for future immunological analysis.

TABLE 4

| Group | N | Recipient haplotype | Dose # of islets | Implant Sites | Duration of Transplant |
|---|---|---|---|---|---|
| 1a | 3 | RT1-1 | 6000 | IP/kidney | 3 weeks |
| 1b | 3 | RT1-1 | 6000 | IP/kidney | 3 weeks |
| 1c | 3 | RT1-1 | 6000 | IP/kidney | 3 weeks |
| 2a | 3 | RT1-1 | 6000 | IP/kidney | 3 weeks |
| 2b | 3 | RT1-1 | 6000 | IP/kidney | 3 weeks |
| 2c | 3 | RT1-1 | 6000 | IP/kidney | 3 weeks |
| 3a | 3 | RT1-1 | 6000 | IP/kidney | 3 weeks |
| 3b | 3 | RT1-1 | 6000 | IP/kidney | 3 weeks |
| 3c | 3 | RT1-1 | 6000 | IP/kidney | 3 weeks |
| 4a | 3 | RT1-1 | 6000 | IP/kidney | 3 weeks |

TABLE 4-continued

| Group | N | Recipient haplotype | Dose # of islets | Implant Sites | Duration of Transplant |
|---|---|---|---|---|---|
| 4b | 3 | RT1-1 | 6000 | IP/kidney | 3 weeks |
| 4c | 3 | RT1-1 | 6000 | IP/kidney | 3 weeks |

In Groups 1 and 4, no changes in the diabetic state are measured. In Group 4, rejection occurs in the expected two week time frame as measured by a transient normoglycemia followed by a return to the diabetic state. In Group I, a more rapid rejection of the implant due to sensitization of the recipients occurs. In the recipients previously exposed to tolerizing doses of encapsulated WF islets (Groups 2 and 3), islet cells survive and result in a continuous maintenance of normoglycemia.

EXAMPLE 3

Use of Encapsulated Islets for Induction of Allograft Tolerance in Humans

Human islets are isolated from cadavers and 1,500 islets/kg body weight are PEG-encapsulated and implanted under the kidney capsule in a diabetic patient. After two months, a curative dose of 15,000 unencapsulated islets/kg body weight are injected intraportally. Insulin administration is continued during the course of the protocol up to administration of the curative dose. Blood glucose levels are constantly monitored and are within the normal range.

EXAMPLE 4

Treatment of Parkinson's Disease (Xenograft)

Adrenal chromaffin cells are isolated from inbred baboon adrenal glands and 1,000 cell/kg body weight are encapsulated in an appropriate PEG conformal coating. The capsule is implanted into the interstitial brain region of a human by a neurosurgeon using stereotaxic instruments. After 1 month of tolerization, 10,000 unencapsulated cells/kg body weight are injected into the same brain region. Significant improvement in the condition is observed.

EXAMPLE 5

Prevention of Hemophilia

A male individual at risk of developing hemophilia, an x-linked disorder, by virtue of family history, is subjected to genetic screening to determine the presence or absence of the gene encoding Factor VIII, and to clotting time analysis. If the gene is absent or clotting time is reduced, 2,500 liver cells/kg recipient body weight are isolated from a human donor and encapsulated in a PEG conformal coating. The encapsulated cells are implanted under the kidney capsule. One month later, 5,000 cryopreserved liver cells/kg recipient body weight (from the same donor) are injected intraportally. Clotting time is significantly improved.

EXAMPLE 6

Liver Transplant (Xenograft)

An individual in need of a liver transplant is subcutaneously implanted with 1,000 PEG-encapsulated liver cells/kg body weight isolated from an inbred baboon. Two months later, the entire liver is transplanted into the individual. Signs of organ rejection and vital signs are monitored over several months. Rejection does not occur.

EXAMPLE 7

Prevention of Myasthenia Gravis (Xenograft)

Myasthenia gravis is an autoimmune disorder resulting from the presence of antibodies against the acetylcholine receptor on neurons. An individual having very early signs of the disease is implanted under the kidney capsule with a tolerizing dose of 2,500 PEG-encapsulated neural cells/kg recipient body weight expressing the acetylcholine receptor isolated from baboons. This results in tolerization to the acetylcholine receptor and prevention of the disorder.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of treating diabetes in a mammal in need thereof, comprising the steps of:
    implanting in said mammal a tolerizing dose of insulin-secreting cells encapsulated in a biologically compatible permselective membrane, wherein said implanting step is subcapsular, subcutaneous, intraperitoneal or intraportal; then
    administering to said mammal a therapeutic dose of corresponding unencapsulated insulin-secreting cells.

2. The method of claim 1, wherein said mammal is a human, canine or feline.

3. The method of claim 1, wherein said tolerizing dose is one to two orders of magnitude less than said therapeutic dose.

4. The method of claim 1, wherein said insulin-secreting cells are pancreatic islet cells.

5. The method of claim 1, wherein said membrane comprises polyethylene glycol.

6. The method of claim 1, wherein said tolerizing and therapeutic doses comprise porcine cells.

7. The method of claim 1, further comprising the step of administering one or more anti-inflammatory agents to said mammal prior to, at the same time as, or subsequent to administration of said therapeutic dose.

8. The method of claim 1, wherein said membrane has a molecular weight cutoff of about 150 kDa or less.

9. The method of claim 1, wherein said membrane has a pore size of less than about 0.4 µm.

10. The method of claim 9, wherein said membrane has a pore size of less than about 0.2 µm.

11. The method of claim 1, wherein said therapeutic dose is between one and two orders of magnitude higher than said tolerizing dose.

12. The method of claim 1, wherein said administering step is intraperitoneal, intraportal or subcutaneous.

13. The method of claim 1, wherein said tolerizing dose is administered incrementally.

* * * * *